United States Patent
Sun (10) Patent No.: US 7,931,866 B2
(45) Date of Patent: Apr. 26, 2011

(54) MICELLE-CONTROLLED NANOPARTICLE SYNTHESIS FOR SERS

(75) Inventor: Lei Sun, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 12/370,413

(22) Filed: Feb. 12, 2009

(65) Prior Publication Data
US 2009/0148675 A1    Jun. 11, 2009

Related U.S. Application Data (62) Division of application No. 10/794,996, filed on Mar. 4, 2004, now Pat. No. 7,560,285.

(51) Int. Cl.
G01N 21/65 (2006.01)
G01J 3/44 (2006.01)

(52) U.S. Cl. .................. 422/82.05; 356/301; 422/82.09; 422/99; 436/37; 436/86; 436/91; 436/96; 436/164; 436/171; 436/183; 436/524; 436/525

(58) Field of Classification Search .............. 422/56–58, 422/82.05–82.09, 82.11, 99; 436/37, 86, 436/91, 96, 106, 164, 171, 183, 518, 524–525; 356/301
See application file for complete search history.

(56) References Cited

OTHER PUBLICATIONS

Seregina, M. V. et al, Chemistry of Materials 1997, 9, 923-931.*
Willert, M. et al, Chemistry of Materials 2001, 13, 4681-4685.*
Niessen, H. G. et al, Journal of Molecular Catalysis A: Chemical 2002, 182-183, 463-470.*
Chen, C.-W. et al, Chemistry of Materials 2002, 14, 2232-2239.*
Sohn, B.-H. et al, Journal of the American Chemical Society 2003, 125, 6368-6369.*
Abes, J. I. et al, Materials Science and Engineering C 2003, 23, 641-650.*
Smid, J., Industrial and Engineering Chemistry Product Research and Development 1980, 19, 364-371.*
Andrews, M. P. et al, Chemistry of Materials 1989, 1, 174-187.*
Antonietti, M. et al, Angewandte Chemie International Edition, English 1997, 36, 910-928.*
Loppacher, C. et al, Macromolecules 2002, 35, 1936-1940.*
P.F. Liao, et al.; Chemical Physics Letters; 1981; No. 82; pp. 355-359.
P.F. Liao, et al.; Optics Letters; 1982; No. 7; pp. 483-485.
T. Vo-Dinh, et al.; Proceedings-APCA Annual Meeting; 1985; vol. 6; pp. 85-81.3.
J.P. Goudonnet, et al.; Chemical Physics; 1986; No. 106; pp. 225-232.
T. Vo-Dinh, et al.; Analytica Chimica Acta; 1986; No. 181; pp. 139-148.

(Continued)

*Primary Examiner* — Arlen Soderquist
(74) *Attorney, Agent, or Firm* — Pillsbury Winthrop Shaw Pittman LLP (57) ABSTRACT

The methods and apparatus disclosed herein concern nanoparticle layers uniformly distributed on a surface or substrate. In certain embodiments of the invention, the nanoparticle layers are of use for Raman spectroscopy. In certain embodiments of the invention, a micelle-metal ion complex is formed and deposited on a surface. The polymer component of the micelle-metal ion complex may be removed resulting in formation of nanoparticles of a uniform size and distribution. The polymers may contain one or more ligands. The number and type of ligands in a micelle will determine the type and amount of metal ion bound to the micelle, in turn determining the metal composition and size of the nanoparticles. The distribution micelle-metal ion complexes on a surface may determine the distribution and periodicity of the nanoparticle layer. In other embodiments, rod or columnar-shaped nanoparticles may be generated. Other embodiments concern the generation of uniform alloy nanoparticles.

11 Claims, 4 Drawing Sheets

OTHER PUBLICATIONS

P.D. Enlow, et al.; Analytical Chemistry; 1986; No. 58, pp. 1119-1123.
B.K. Russell, et al.; Physical Review B; 1987; No. 35; pp. 2151-2154.
A.H.R. Al-Obaidi, et al.; Journal of Physical Chemistry; 1994; pp. 11163-11168.
A. Roescher, et al.; Polymeric Materials Science & Engineering; 1995; pp. 283-284.
J.P. Spatz, et al.; Advanced Materials; 1996; No. 8; pp. 337-340.
C. Sangregorio, et al.; Langmuir; 1996; No. 12; pp. 5800-5802.
S.T. Selvan, et al.; Advanced Materials; 1998; No. 10; pp. 132-134.
J.P. Spatz, et al.; Journal of Luminescence; 1998; Nos. 76-77; pp. 168-173.
M.P. Pileni; Supramolecular Science; 1998; No. 5; pp. 321-329.
J.P. Spatz, et al.; Advanced Materials; 1999; No. 11; pp. 149-153.
A. Taleb, et al.; Physical Review B; 1999; No. 59; pp. 13350-13358.
L. Bronstein, et al.; Chemistry of Materials; 1999; No. 11, pp. 1402-1405.
S.T. Selvan, et al.; Journal of Physical Chemistry B; 1999; No. 103; pp. 7441-7448.
K. Seeger, et al.; Journal of Physics D: Applied Physics; 1999; No. 32; pp. L129-L132.
P.A. Lewis, et al.; Journal of Vacuum Science & Technology B; 1999; No. 17; pp. 3239-3243.
T. Tada, et al.; Japanese Journal of Applied Physics—Part 1; 1999; No. 38; pp. 7253-7256.
J.P. Spatz, et al.; Langmuir 2000; No. 16; pp. 407-415.
M.P. Pileni; Pure and Applied Chemistry 2000; No. 72; pp. 53-65.
B. Koslowski, et al.; Journal of Applied Physics 2000; No. 87; pp. 7533-7538.
L.M. Bronstein, et al.; Journal of Catalysis 2000; No. 196; pp. 302-314.
M.L. Wu, et al.; Langmuir 2001; No. 17; pp. 3877-3883.
A. Wellner, et al.; Microelectronic Engineering 2001; Nos. 57-58; pp. 919-924.
B.H. Sohn, et al.; Journal of American Chemical Society 2001; No. 123; pp. 12734-12735.
B.L. Frankamp et al.; Journal of the American Chemical Society 2002; No. 124; pp. 892-893.
Y. Boontongkong, et al.; Macromolecules 2002; No. 35; pp. 3647-3652.
J.H. Youk, et al.; Langmuir 2002; No. 18; pp. 2455-2458.
V. Z-H. Chan, et al.; Materials Research Society Symposium Proceedings 2002; No. 676; pp. Y4.4.1-Y4.4.6.
V.V. Poborchii, et al.; Optics Communications 2002; No. 210; pp. 285-290.
S. Liu, et al.; Langmuir 2002; No. 18; pp. 8350-8357.
M.S. Pio, et al.; Materials Research Society Symposium Proceedings 2002; No. 729; pp. 179-184.
J.P. Spatz, et al.; Advanced Materials 2002; No. 14; pp. 1827-1832.
V. Poborchii, et al.; Applied Physics Letters 2003; No. 82; pp. 508-510.
R. Glass, et al.; Advanced Functional Materials 2003; No. 13; pp. 569-575.
R. Glass, et al.; Nanotechnology 2003; No. 14; pp. 1153-1160.
M-V. Meli, et al.; Langmuir 2003; No. 19; pp. 9097-9100.
Q. Song, et al.; Journal of Nanoparticle Research 2000; No. 2; pp. 381-385.
W. Huang, et al.; Nanotechnology 2003; No. 14; pp. 1075-1080.
M. Antonetti, et al.; Macromolecules 1996; No. 29; pp. 3800-3806.
M. Moeller, et al.; Polymeric Materials Science and Engineering 1999; No. 80; pp. 3-4.
P. Persigehl, et al.; Macromolecules 2000; No. 33; pp. 6977-6981.

* cited by examiner

MICELLE-CONTROLLED NANOPARTICLE SYNTHESIS FOR SERS

CROSS-REFERENCE TO RELATED APPLICATIONS

This is a divisional of U.S. application Ser. No. 10/794,996, filed Mar. 4, 2004, now U.S. Pat. No. 7,560,285. The aforementioned application is incorporated herein by reference in its entirety.

FIELD

Figure 3:
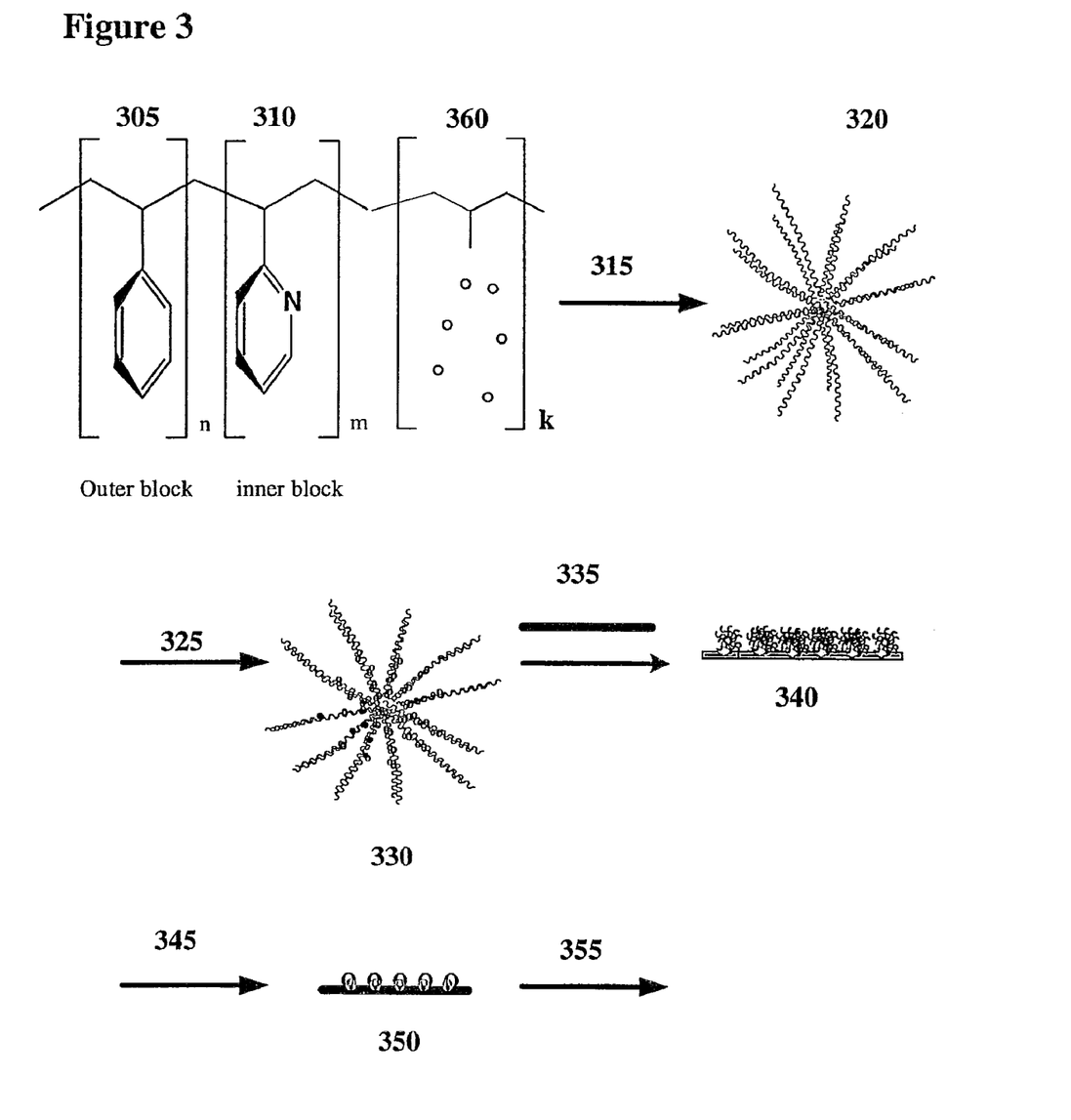
FIG. 3 illustrates an exemplary method for generating a uniform layer of alloy nanoparticles 350.

The disclosed methods may also be used to make alloy nanoparticles 350 with fixed element ratios, size and distribution (FIG. 3). For example, block polymer molecules 305 may be designed to contain two or more different ligands 310, 360, such as crown ethers. The resulting heteropolymer 305, 310, 360 will bind two or more different metal ions 325, for example $Ag^+$, $Cu^{2+}$, $Fe^{3+}$, $Al^{3+}$, $Pd^{2+}$, $Fe^{2+}$, $Ru^{3+}$, $Au^+$, $Au^{3+}$, cyclopentadienyl-iron-tricarbonyl $[CpFe(CO)_3]^+$ cyclopentadienyl-ruthenium-tricarbonyl $[CpRu(CO)_3]^+$, hexachlorostannate (IV) $[SnCl_6]^{2-}$, hexachlororhodate(III) $[RhCl_6]^{3-}$, permolybdate $[MoO_4]^{2-}$, dicyanocuprate(I) ion $[Cu(CN)_2]^-$, perrheniate$[ReO_4]^-$, tetrachloroaurate (III) $[AuCl_4]^-$, dicyanideagenate (I) $[Ag(CN)_2]^-$, hexachloroplatinate (IV) $[PtCl_6]^{2-}$, and tetrahydroxoaluminate (III) $[Al(OH)_4]^-$. After deposition and reduction 345, alloy nanoparticles 350 with a fixed element ratio will form. Such nanoparticles 350 may be used as a SERS substrate 355 or as catalysts for various chemical reactions 355. For example, Au/Pd alloy nanoparticles 350 may be used as alkene hydrogenation catalysts 355, Cu—Pd alloy particles may be used as catalyst for Suzuki coupling reaction (Thathagar et al, J. of Am. Chem. Soc, 124, 2002, p 11858-11859). Pd—Rh alloy particles may be used as hydrogen oxidation catalyst for fuel cells (Christoffersen, et al, Journal of Catalysis 199, 2001, p 123-131). The ratios of the metal ions of the alloy will vary depending on the reaction. For example, A Pd—Ru alloy may range from a ratio of 150:1,100:1, 50:5, 10,1 etc depending on the reaction. In a preferred embodiment of the invention, a Pd—Ru alloy of about 85:15 ratio may be used for methanol oxidation (Hoster et al, Phys. Chem. Chem. Phys., 2001, p 337-346).

BACKGROUND

The SERS (surface enhanced Raman spectroscopy) effect arises from an electromagnetic enhancement of optical processes near noble metal surfaces. The magnitude of the enhancement varies from metal to metal and depends on the surface preparation. Silver shows the largest enhancement, on the order of $10^6$ to $10^7$ increased Raman signal strength.

Previous SERS methods only work well for a limited class of analyte molecules. SERS sensors have been made for organic compounds, metal ions, pH, and $CO_2$ detection with good sensitivity and selectivity. A need exists for methods to produce sensitive and selective Raman sensors for use with other types of analytes.

A problem with SERS technology has been the lack of reproducibility of the surfaces used for surface enhancement. In particular, the reproducible production of surfaces uniformly coated with metal or metal alloy nanoparticles has been difficult to achieve. The synthesis of metal colloids can be unpredictable, resulting in nanoparticles of varying sizes that make SERS detection unreliable. In addition, surface chemistry has been limiting with respect to production of surfaces containing multiple Raman-active metals. The generation of Raman surfaces with even low levels of periodicity, allowing fine-tuning of surfaces for detecting different analytes, has been expensive to scale-up.

Recent advances in electron-beam, ion-beam, and scanning probe lithography techniques have pushed the minimum size of microfabricated structures below the 100 nm scale. However, generation of homogeneous nanoparticle layers has not progressed equivalently. A reliable and reproducible method is needed to generate uniform nanoparticle surfaces for use in Raman spectroscopy. Such uniform nanoparticle surfaces could be used in combination with microfabricated structures to provide the surfaces for the sensitive and reliable detection of a wide range of analytes.

BRIEF DESCRIPTION OF THE DRAWINGS

The following drawings form part of the present specific metal ion and are included to further demonstrate certain aspects of the disclosed embodiments of the invention. The embodiments may be better understood by reference to one or more of these drawings in combination with the detailed description of specific embodiments presented herein.

DESCRIPTION OF ILLUSTRATIVE EMBODIMENTS

The following detailed description contains numerous details in order to provide a thorough understanding of the disclosed embodiments of the invention. However, it will be apparent to those skilled in the art that the embodiments may be practiced without these specific details. In other instances, devices, methods, procedures, and individual components that are well known in the art have not been described in detail herein.

DEFINITIONS

A "block polymer" is a polymer whose molecules consist of blocks that are linearly connected together. The blocks may be connected directly or through a linking unit that is not part of the blocks. The individual blocks that form a polymer molecule may be identical (homopolymer) or may be different (heteropolymer). Heteropolymers may comprise, for example, some blocks that are charged (e.g., anionic) and some blocks that are uncharged. Heteropolymers may also comprise some blocks that are hydrophobic and some that are hydrophilic in nature. Where micelles are to be exposed to a nonpolar solution, the constituent heteropolymers may contain hydrophobic outer blocks and hydrophilic or charged inner blocks.

As used herein, "a" or "an" may mean one or more than one of an item.

As used herein, an "analyte" may refer to any atom, chemical, molecule, compound, composition or aggregate of interest for detection and/or identification. Non-limiting examples of analytes include an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant. In certain embodiments of the invention, one or more analytes may be labeled with one or more Raman labels.

Uniform Nanoparticle Layers

Figure 1:
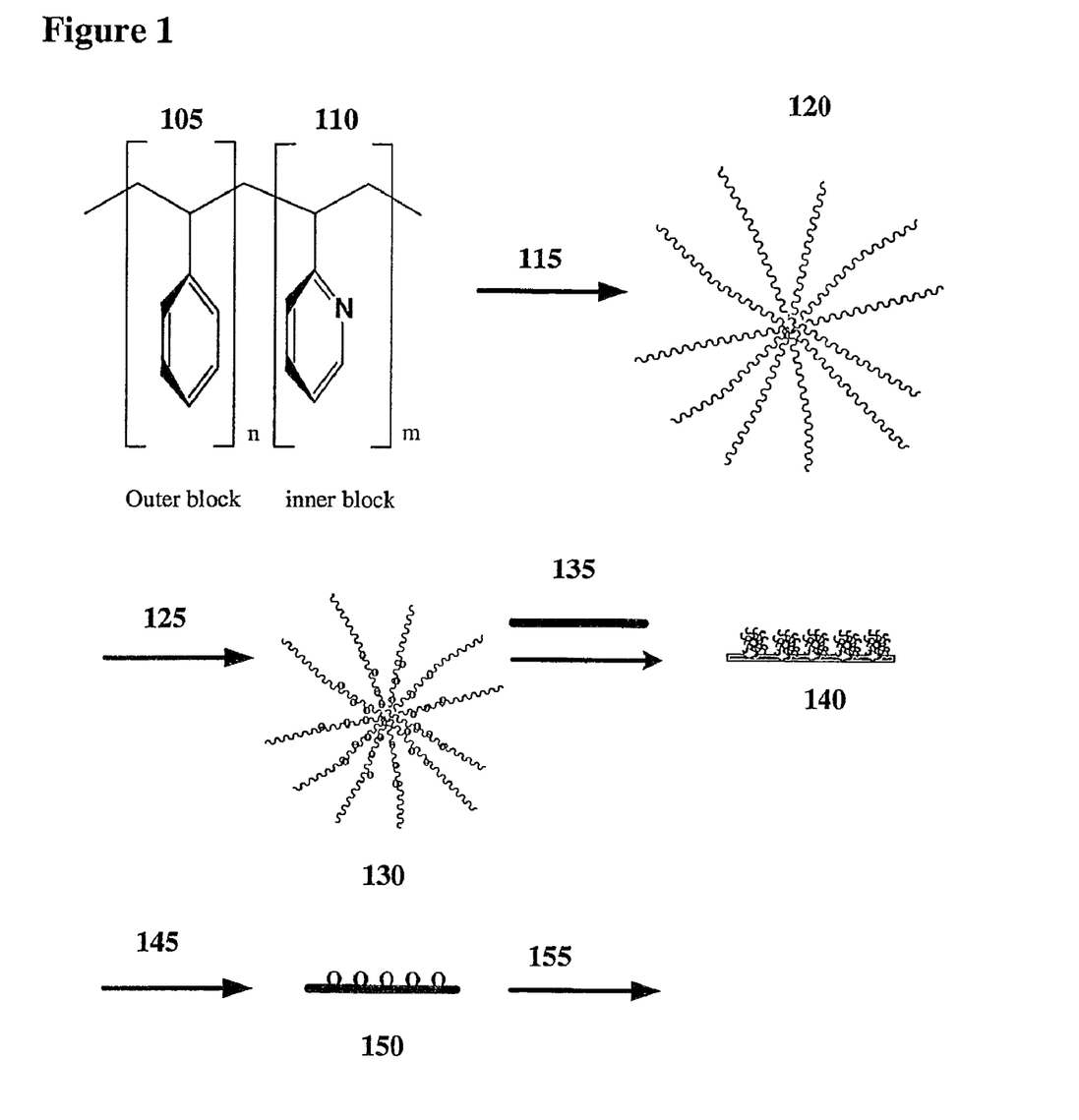
FIG. 1 illustrates an exemplary method for generating a uniform layer of nanoparticles 150 on a surface 135.

Certain embodiments of the invention concern methods for generating uniform nanoparticle layers 150 from micelle-metal ion complexes 130 (FIG. 1). The micelles 120 may be formed from block polymer molecules 105 incorporating one or more ligands 110. The ligands 110 provide can bind to a predetermined number of metal ions 125 for each micelle-metal ion complex 130, controlling the size and composition of the nanoparticles 150 formed. In particular embodiments, a layer of spherical nanoparticles 150 that exhibit uniform size and periodicity may be produced. Advantages over the known methods of nanoparticle 150 production include the ability to generate a nanoparticle layer 150 with a precise periodicity for use in Raman detection methods.

As shown in FIG. 1, block polymers 105 comprising ligands 110 may be used to generate a micelle 120, for example by self-assembly after exposure to a non-polar solution 115. The micelle 120 may be combined with one or more metal ions 125 to generate a micelle-metal ion complex 130. In certain embodiments, the micelle-metal ion complexes 130 are layered on a surface 135 and then the polymer molecules 105, 110 are destroyed, for example by hydrogen plasma 145. At the same time, the metal ions are reduced to solid metal to form nanoparticles 150. Because the number of metal ions incorporated into each nanoparticle 150 may be controlled by the size of the micelles 120 and the density of ligands 110 attached to the polymer molecules 105, the result is a uniform layer of nanoparticles 150 deposited on the surface. In some embodiments, the uniform nanoparticle layer 150 may be used for Raman detection 155.

In other embodiments of the invention (FIG. 2), the disclosed methods may be used to generate a uniform surface of rod or pillar-shaped nanoparticles 260. The nanoparticles 260 may be of uniform size, height and periodicity. In some embodiments, the rod or pillar-shaped nanoparticles 260 may be formed using a bilayered substrate 240, comprising a first surface 235 and a second surface 270. The top (first) surface 235 may be of a predetermined thickness to allow generation of rods or pillars 260 of a selected height. In various embodiments, the first surface 235 may comprise a Raman active metal, such as silver (Ag), gold (Au), platinum (Pt), aluminum (Al) or copper (Cu).

Figure 2:
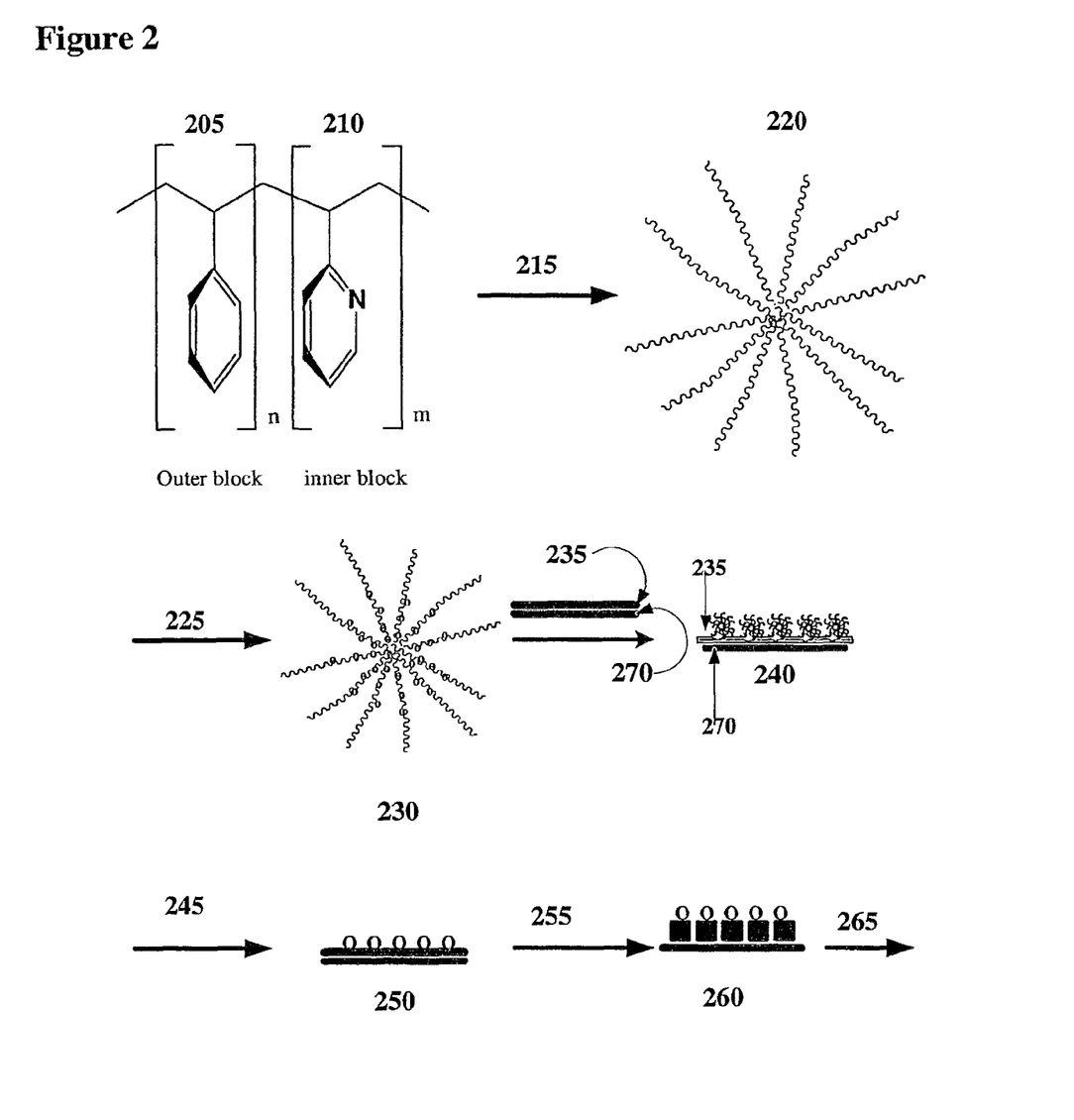
FIG. 2 illustrates an exemplary method for generating a uniform rod or pillar-shaped nanoparticle surface 260.

A uniform layer of nanoparticles 250 may be deposited on top of the first surface 235. The nanoparticle layer 250 may be comprised of a non-reactive metal, such as gold. Reactive ion etching (RIE) 255 or other etching techniques known in the art may be used to etch the first surface 235 around the gold nanoparticles 250. Using RIE 255, the areas of the first surface 235 underlying the gold nanoparticles 250 remain intact, while the remaining areas are etched down to the lower (second) surface 270. Such methods may be used to generate a uniform rough surface 260 of use for Raman detection. The surface 260 may be analyzed by TEM (transmission electron microscopy) or SEM (scanning electron microscopy) to confirm the dimensions and periodicity of the nanoparticles 260. An advantage to using micelle-controlled synthesis of a uniform nanoparticle layer 250 with semi-conductor manufacturing processes (i.e. hydrogen plasma treatment 245 and RIE 255) is that it provides a cheap, controllable, and scalable process for generating Raman substrates 260 of use with a wide variety of analytes.

As shown in FIG. 2, block polymers 205 incorporating ligands 210 are used to generate a micelle 220, for example by self-assembly after exposure to a non-polar solution 215. The micelle 220 may be combined with one or more metal ions 225 to generate micelle-metal ion complexes 230. The micelle-metal ion complexes 230 may be layered on top of a first surface 235 that overlies a second surface 270, to form a micelle-metal ion complex layer 230 on top of a bilayered substrate 240. The polymer molecules 205, 210 may be destroyed, for example by hydrogen plasma treatment 245 to form a nanoparticle layer 250 on top of the first surface 235. The bilayered substrate 240 and attached nanoparticles 250 may be exposed to an etching process 255, such as RIE. The etching process 255 removes the areas of the first surface 235 around the gold nanoparticles 250, leaving a uniform substrate comprised of pillar or rod-shaped composite nanoparticles 260. In various embodiments of the invention, the pillar or rod-shaped nanoparticles 260 form a Raman active substrate with a uniform height, size and periodicity. Such substrates 260 may be used for Raman detection of analytes 265.

The disclosed methods may also be used to make alloy nanoparticles 350 with fixed element ratios, size and distribution (FIG. 3). For example, block polymer molecules 305 may be designed to contain two or more different ligands 310, 360, such as crown ethers. The resulting heteropolymer 305, 310, 360 will bind two or more different metal ions 325, for example [AuCl$_4$]$^-$. After deposition and reduction 345, alloy nanoparticles 350 with a fixed element ratio will form. Such nanoparticles 350 may be used as a SERS substrate 355 or as catalysts for various chemical reactions 355. For example, Au/Pd alloy nanoparticles 350 may be used as alkene hydrogenation catalysts 355, Cu—Pd alloy particles may be used as catalyst for Suzuki coupling reaction (Thathagar et al, J. of Am. Chem. Soc, 124, 2002, p 11858-11859). Pd—Rh alloy particles may be used as hydrogen oxidation catalyst for fuel cells (Christoffersen, et al, Journal of Catalysis 199, 2001, p 123-131). The ratios of the metal ions of the alloy will vary depending on the reaction. For example, A Pd—Ru alloy may range from a ratio of 150:1, 100:1, 50:5, 10, 1 etc depending on the reaction. In a preferred embodiment of the invention, a Pd—Ru alloy of about 85:15 ratio may be used for methanol oxidation. (Hoster et al, Phys. Chem. Chem. Phys., 2001, p 337-346).

The size of the alloy nanoparticles 350 may be controlled by the amount of metal ion 325 bound to each micelle 320. Metal ion binding 325 may in turn be determined by controlling the size of the micelle 320 and the density of ligands 310, 360 in the micelle 320. The average distance between nanoparticles 350 may be determined by the size of the micelles 320. In addition, several different types of metallic nanostructures may be used for SERS (see Table 1).

As shown in FIG. 3, nanoparticles 350 may be generated using two or more different metal ions 325 bound to each micelle 320. Block polymers 305 incorporating at least two different types of ligand 310, 360 may be used to generate a micelle 320, for example by self-assembly after exposure to a non-polar solution 315. The micelle 320 may be combined with at least two different types of metal ion 325 to generate micelle-mixed metal ion complexes 330. The micelle-mixed metal ion complexes 330 may be layered on top of a surface 335 and the polymer molecules 305, 310, 360 destroyed, for example by hydrogen plasma treatment 345. This results in the production of metal alloy nanoparticles 350 comprising two or more different metals. Because the ratio of metals in the alloy may be controlled by the density of each type of ligand 310, 360 in the micelle 320, the alloy nanoparticles 350 may be designed to contain any ratio of two or more metals. Thus, where the alloy nanoparticle substrate 350 is used for Raman detection, the alloy composition may be precisely controlled to optimize the Raman spectroscopic properties for each type of analyte to be detected.

In alternative embodiments of the invention, the alloy nanoparticle substrate 350 may be used as a catalyst for a reaction 355, for example using mixed gold/platinum nanoparticles 350 as an alkene hydrogenation catalyst 355.

In various embodiments of the invention, the nanoparticle substrates 150, 250, 260, 350 may be used to determine the optimal height, periodicity, size or metal alloy composition of nanoparticles 150, 250, 260, 350, to be used for a given Raman spectroscopy procedure. It is expected that the optimal nanoparticle substrate 150, 250, 260, 350 characteristics will vary, depending on the Raman modality used, the type of analytes to be detected, and the characteristics of the sample or medium to be analyzed. For example, where very large analytes, such as bacteria, virus or other pathogens are to be identified, the periodicity of the nanoparticle substrate 150, 250, 260, 350 may be increased to allow the analytes to penetrate the nanoparticle layer 150, 250, 260, 350. A close juxtaposition between nanoparticles 150, 250, 260, 350 and analytes will generally result in a larger enhancement of surface-enhanced Raman signals.

Micelles

In various embodiments of the invention, micelles may serve a multiplicity of purposes for formation of uniform nanoparticle layers. In some embodiments, micelles may be used to control the distribution, periodicity, density and composition of nanoparticles deposited on a surface. Micelle structure will itself be determined, in large part, by the types and compositions of polymer molecules used to form the micelle and the solvent environment of the micelle. As described above, heteropolymeric molecules may be obtained, in which the outer blocks of the polymer are relatively hydrophobic in nature and the inner blocks are hydrophilic. When placed in a non-polar solvent, the polymer molecules will spontaneously self-assemble into micelles, with the hydrophobic blocks on the outer surface of the micelle and hydrophilic blocks inside. The hydrophilic interiors of the micelles create an aqueous environment that selectively partitions in charged or polar species, such as metal ions.

The hydrophilic blocks may contain one or more attached ligands. The ligands may bind to specific metal ions. As discussed further below, the type of ligand attached to the polymer molecule will determine which metal ions can bind to the micelle, while the density of ligands in the micelle and the size of the micelle will determine how many metal ions are bound per micelle. A uniform distribution of micelle size and ligand density will result in uniformity of the number of metal ions in each micelle. The number of metal ions per micelle will in turn determine the distribution of the metal nanoparticles that form when metal ions are reduced. Thus, use of very homogeneous micelle-metal ion complexes will result in formation of a homogeneous size population of metal nanoparticles, with generally one nanoparticle formed per micelle. The distribution of nanoparticles on a surface will vary as a function of the size, structure and density of micelles in the non-polar solvent and the method of depositing micelles on the surface. A maximum nanoparticle density will be achieved where the micelles are packed on the surface in a contiguous array (i.e., touching). Such factors may be strictly controlled to produce a precisely distributed layer of nanoparticles on a surface. In certain embodiments, the micelles may form hexagonal arrays on the substrate surface, resulting in a hexagonal pattern of deposited nanoparticles. The nanoparticles formed by micelle techniques may range in size from about 1 nm to about 200 nm in diameter.

Exemplary heteropolymers that may be used to provide micelles include, but are not limited to, polystyrene-poly(4-vinylpyridine); polystyrene-poly(2-vinylpyridine); polystyrene-poly(4-vinylphenol); poly(4-vinylpyridine-co-butyl methacrylate); poly(styrene-co-maleic acid); and poly(vinyl chloride-co-vinyl acetate-co-maleic acid). Another exemplary heteropolymer that may be used is poly(N-vinyl-2-pyrrolidone) and poly(D,L-lactide) (PVP-b-PDLLA). The heteropolymer may be synthesized by ring-opening polymerization of D,L-lactide, initiated by potassium PVP hydroxylate or other known techniques. PVP-b-PDLLA is capable of self-assembling into polymeric micelles with multiple binding sites and has high entrapment efficiency Self-assembling heteropolymers incorporating blocks of different polarity have been used to make micelles (Haupt, et. al. J. of Applied Physics, 91, p 6057-6059). The heteropolymers may be dissolved in non-polar solvents, for example toluene ($C_6H_5CH_3$), benzene ($C_6H_6$), carbon tetrachloride ($CCl_4$) or diethyl ether ($CH_3CH_2OCH_2CH_3$). The heteropolymers spontaneously arrange themselves into micelles in such solvents, due to the tendency of the heteropolymers to arrange themselves so as to minimize the exposure of hydrophilic blocks to the non-polar solvent. Such methods of micelle formation are analogous to the well-known tendency of biological lipids, such as phospholipids, to form micelles in aqueous solution. In the case of lipid micelles in water, the polar head groups are oriented on the outside of the micelle, where they are exposed to the polar medium, while the hydrophobic tails of the lipid molecules are located in the center of the micelle.

Production of iron nanoparticles using micelle-mediated reduction has been reported (Su et al, J. Phy. Chem. B, 2000, 104:6505-6508; Li et al, Chem. Mater., 2001, 13:1008-1014). However, the nanoparticles that were produced were not arranged on a substrate surface in an ordered array and were not suitable for use with Raman spectroscopy. Earlier reports also did not control the ligand content of the polymer molecules to regulate the metal ion content of the micelles.

In the methods disclosed herein, the ligand content of the micelles may be regulated by controlling the number and type of ligand blocks in the heteropolymer. The size of the micelles may be regulated by controlling the heteropolymer size (molecular weight). The ligand content of the micelles will in turn determine the number and type of metal ions that can bind per micelle and the metal composition and size of the nanoparticles formed. The size of the micelles will affect both the size of the nanoparticles and the distribution of nanoparticles on the substrate. Methods of making block polymer molecules are known in the art (e.g. "Block Copolymers: Synthetic Strategies, Physical Properties, and Applications", Nikos Hadjichristidis, Stergios Pispas, George Floudas) Block polymer molecules may also be obtained from commercial sources, such as Sigma-Aldrich Inc. and Polymer Source Inc.

In certain embodiments of the invention, the metal ion affinity of the micelles may be controlled by adjusting the ligand content of the heteropolymers. Different ligands exhibit different specificities and binding affinities for different metal ions. The affinities of different types of ligands for various metal ions are well known in the art.

Micelle-metal ion complexes may be deposited on a surface, for example by dip coating or spin coating. In certain embodiments of the invention, micelle-metal ion complexes may be deposited on a silicon (Si) or metal-coated silicon surface to form a mono-micellar film. In various embodiments, the deposited mono-micellar film may be treated with an agent to remove the polymer molecules. For example, hydrogen-plasma treatment will destroy and remove the polymer molecules, as well as reducing the metal ions to metal atoms. The final products are deposited as uniformly spaced nanoparticles on the substrate surface. In certain embodiments, spherical nanoparticles may be formed by depositing micelle-metal ion complexes on an inert substrate, followed by polymer removal and metal ion reduction.

In other embodiments of the invention, rod and/or pillar-shaped nanoparticles may provide more optimal Raman spectroscopy characteristics than spherical nanoparticles. Micelle-metal ion complexes may be deposited onto metal-coated substrates and reduced. In such cases, the metal coating may comprise a thin first surface of silver, platinum, aluminum or copper on top of a second, thicker surface of a standard chip substrate, for example silicon or aluminum. After reduction and deposit of, for example, gold nanoparticles on top of a metal first surface, the gold nanoparticles can be used as a mask protecting the underlying first surface from etching by techniques such as RIE (reactive ion etching), discussed below. RIE may be used to remove portions of the first surface that are not protected by gold nanoparticles, resulting in formation of rod or pillar-shaped nanoparticles. The rods or pillars will contain, for example, a composite of gold on top of the pillar and silver or other Raman-active metal below. This method may be used to control the dimensions of the nanoparticle substrate, by regulating the size and distribution of gold nanoparticles on the first surface before etching, the thickness of the first surface and the time of exposure to RIE. The thickness of the metal first surface may range from about 10 to about 200 nm.

Hydrogen Plasma-Reactive Ion Etching

In some embodiments of the invention, hydrogen plasma treatment may be used to remove the polymer components of micelle-metal ion complexes (see, e.g. Haupt et al., 2002; Boyen et al., 2002). Hydrogen plasma treatment does not leave any film that could interfere with the use of the nanoparticle substrate for Raman spectroscopy. In a non-limiting example, a 15-minute exposure to hydrogen plasma at about 100 W and 1 mbar of pressure may be used to remove polymer molecules and reduce metal ions to form metal nanoparticles.

In other embodiments of the invention, dry etching techniques such as RIE may be used to remove portions of a surface. In dry etching, reactive gas plasma is used in place of a wet etching solution. Dry etching provides a higher resolution than wet etching, with less "undercutting" of a masked substrate layer. Gaseous etching is generally performed with halogenated compounds that, depending on the substrate, may comprise bromine, chlorine, $SiCl_4$, sulfur hexafluoride $SF_6$ or carbon-tetrafluoride $CF_4$-based gases in a carrier gas.

Plasma etching techniques are known for anisotropic removal of thin film materials. Alternative systems for plasma etching include electron cyclotron resonance (ECR) and reactive ion etching (RIE). Such systems have been routinely used to etch silicon chip substrates, such as silicon dioxide and silicon nitride. In RIE, the plasma form of a gas is used to chemically react with a solid-phase substrate to create volatile products. The products diffuse away, leaving an etched surface. In a non-limiting example, Ag—Si surfaces may be subjected to RIE etching with plasma-phase sulfur hexafluoride using, for example, a Plasma-Therm Model 720 RIE SLR system.

In one embodiment of the invention, nanoparticles may be used to form an etch mask on a substrate. The etch mask and substrate may be further treated to form a uniform, etched nanoparticle substrate layer. In another embodiment, the mask may be transferred to a substrate using low-energy reactive ion-etching (RIE). In another embodiment, the etched nanomask may be removed from the substrate with an aqueous solution (e.g. $Na_2SO_4$, $H_2NCSNH_2$).

In various embodiments of the invention, an etched metal-coated substrate may comprise Au—Si, Ag—Si, Pt—Si, Cu—Si, Al—Si, Au—Al, Ag—Al, or Pt—Al. In certain embodiments, a metal-coated substrate may be Au—Si or Ag—Si. The block polymer structure and the thickness of a metal first layer may be adjusted to form various substrates of narrowly distributed metal nanoparticles. The substrates may be screened in order to optimize the conditions for detection of specific analytes. The substrate structures may be viewed by TEM (transmission electron microscopy) (e.g., Frankamp et al., J. Am. Chem. Soc. 124:892-893, 2002).

Raman Spectroscopy

Raman Detectors

In various embodiments of the invention, uniform nanoparticle layers on a surface or substrate may be used in conjunction with known Raman spectroscopy techniques for a variety of applications, such as identifying and/or quantifying one or more analytes in a sample. Methods of Raman detection are known in the art and any such known method may be used. A non-limiting example of a Raman detection unit of use is disclosed in U.S. Pat. No. 6,002,471. In this embodiment of the invention, the excitation beam is generated by either a Nd:YAG laser at 532 nm wavelength or a Ti:sapphire laser at 365 nm wavelength. Pulsed laser beams or continuous laser beams may be used. The excitation beam passes through confocal optics and a microscope objective, and is focused onto the nanochannel or microchannel containing packed nanoparticles. The Raman emission light from the macromolecule is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal may be detected by a Raman detector. The detector includes an avalanche photodiode interfaced with a computer for counting and digitization of the signal.

Alternative examples of detection units are disclosed, for example, in U.S. Pat. No. 5,306,403, including a Spex Model 1403 double-grating spectrophotometer equipped with a gallium-arsenide (GaAs) photomultiplier tube (RCA Model C31034 or Burle Industries Model C3103402) operated in the single-photon counting mode. The excitation source is a 514.5 nm line argon-ion laser from SpectraPhysics, Model 166, and a 647.1 nm line of a krypton-ion laser (Innova 70, Coherent).

Alternative excitation sources include a nitrogen laser (Laser Science Inc.) at 337 nm and a helium-cadmium laser (Liconox) at 325 nm (U.S. Pat. No. 6,174,677). The excitation beam may be spectrally purified with a bandpass filter (Corion) and may be focused on a nanochannel or microchannel using a 6× objective lens (Newport, Model L6X). The objective lens may be used to both excite the molecule of interest and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as charged injection devices, photodiode arrays or phototransistor arrays.

Any suitable form or configuration of Raman spectroscopy or related techniques known in the art may be used for detection of the macromolecules on the uniform surface, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Raman Labels

Certain embodiments may involve attaching a label to the molecule linked to the nanoparticle surface to facilitate their measurement by a Raman detector. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins and aminoacridine. These and other Raman labels may be obtained from commercial sources (e.g., Molecular Probes, Eugene, Oreg.).

Polycyclic aromatic compounds in general may function as Raman labels, as is known in the art. Other labels that may be of use for particular embodiments include cyanide, thiol, chlorine, bromine, methyl, phosphorus and sulfur. In certain, carbon nanotubes may be of use as Raman labels. Methods of use of labels in Raman spectroscopy are known (e.g., U.S. Pat. Nos. 5,306,403 and 6,174,677).

Micro-Electro-Mechanical Systems (MEMS)

In various embodiments of the invention, uniform nanoparticle substrates may be incorporated into a larger apparatus and/or system. In certain embodiments, the substrate may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (e.g., Voldman et al., Ann. Rev. Biomed. Eng. 1:401-425, 1999). The sensor components of MEMS may be used to measure mechanical, thermal, biological, chemical, optical and/or magnetic phenomena. The electronics may process the information from the sensors and control actuator components such pumps, valves, heaters, coolers, filters, etc. thereby controlling the function of the MEMS.

The electronic components of MEMS may be fabricated using integrated circuit (IC) processes (e.g., CMOS, Bipolar, or BICMOS processes). They may be patterned using photolithographic and etching methods known for computer chip manufacture. The micromechanical components may be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Methods for manufacture of nanoelectromechanical systems may be used for certain embodiments of the invention. (See, e.g., Craighead, Science 290:1532-36, 2000.)

In some embodiments of the invention, uniform nanoparticle substrates may be connected to various fluid filled compartments, such as microfluidic channels, nanochannels and/or microchannels. These and other components of the apparatus may be formed as a single unit, for example in the form of a chip as known in semiconductor chips and/or microcapillary or microfluidic chips. Alternatively, the uniform nanoparticle substrates may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, quartz, etc.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. (See, e.g., Craighead, Science 290:1532-36, 2000.) Various forms of microfabricated chips are commercially available from, e.g., Caliper Technologies Inc. (Mountain View, Calif.) and ACLARA BioSciences Inc. (Mountain View, Calif.).

In certain embodiments of the invention, part or all of the apparatus may be selected to be transparent to electromagnetic radiation at the excitation and emission frequencies used for Raman spectroscopy, such as glass, silicon, quartz or any other optically clear material. For fluid-filled compartments that may be exposed to various analytes, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

Example

Protocol to make Au Nanoparticles

Diblock polymer Polystyrene-block-poly(2-vinylpyridine) may be purchased from Polymer Source, Inc. The polymer is dissolved in hot toluene at approximately 0.5% wt concentration. 5 mM solutions of HAuCl4 of equal volume are added with intense stirring of 1 hour to form the gold-polymer complex. A silicon wafer is dipped into the resulting solution for 5 minutes, and then rinsed with excess cold water twice. The resulting Au-polymer coated wafer is air-dried, and treated with hydrogen-plasma (100 W/1 mbar/10 min). The treated wafer may be used in SERS experiment directly.

Protocol to Test the Au Nanoparticles' SERS Activity:

The SERS measurement was performed on a Raman microscope (Renishaw, UK) equipped with a 514 nm Argon ion laser (25 mW). A Press-to-seal Silicone Isolators (Grace Biolabes) was fixed on top of the silicon wafer. 10 uL of 1 mM Adenine solution was added to the well, and the laser beam was focused on the top surface of the sample while scattering photons were collected for 10-20 second.

Figure 4:
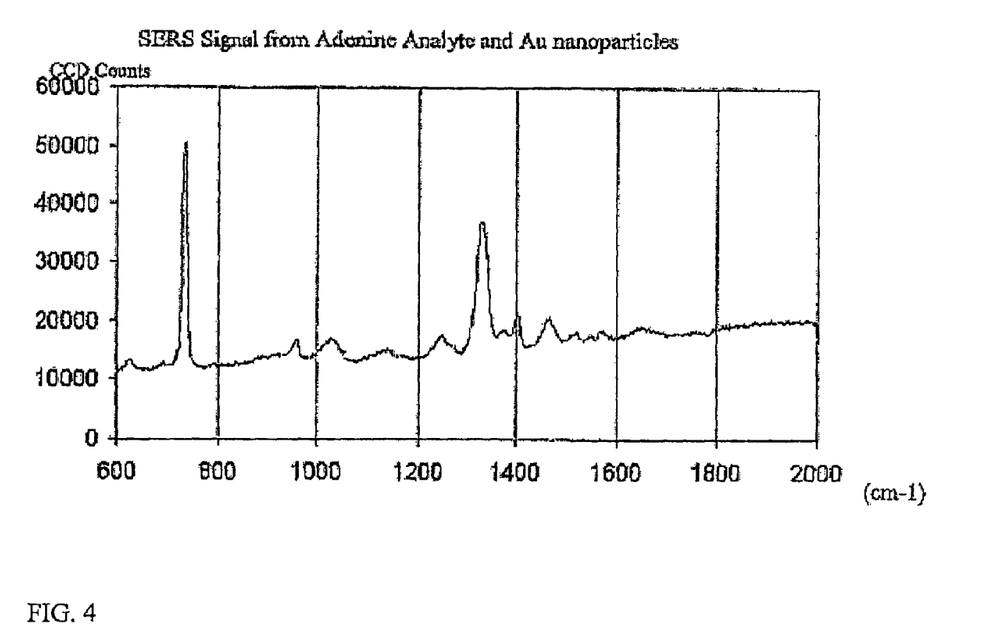
FIG. 4 illustrates the strong SERS enhancement activity of Au nanoparticles produced through micelle-controlled method.

The expected results:

The Au nanoparticles produced through micelle-controlled method demonstrates strong SERS enhancement activity as shown in FIG. 4.

All of the METHODS and APPARATUS disclosed and claimed herein can be made and used without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

The invention claimed is:

1. A micelle-metal ion complex comprising:
    a block polymer comprising three or more blocks having two or more different types of ligands, with at least a first block having a first ligand and a second block having a second ligand; and
    two or more different types of metal ions attached to the two or more different types of ligands, wherein the metal ions are located substantially in a core of the micelle-metal complex,
    the micelle-metal ion complex being made from the block polymer having three or more blocks with at least two or more ligands attached thereto in the core of the micelle to which the two or more metal ions are attached.

2. The micelle-metal ion complex of claim 1, wherein the block copolymer has hydrophobic blocks and hydrophilic blocks and wherein the hydrophobic blocks are located at an outer surface of the micelle and the hydrophilic blocks are located inside the micelle.

3. The micelle-metal ion complex of claim 1, wherein the two or more different ligand bond to specific metal ions.

4. The micelle-metal ion complex of claim 1, wherein the one or more metal ions comprise at least one metal ion selected from the group consisting of $Ag^+$, $Cu^{2+}$, $Fe^{3+}$, $Al^{3+}$, $Pd^{2+}Fe^{2+}$, $Ru^{3+}$, $Au^+$, $Au^{3+}$, cyclopentadienyl-iron-tricarbonyl $[CpFe(CO)_3]^+$, cyclopentadienyl-ruthenium-tricarbonyl $[CpRu(CO)_3]^+$, hexachlorostannate (IV) $[SnCl6]2-$, hexachlororhodate(III) $[RhCl6]3-$, permolybdate $[MoO4]2-$, dicyanocuprate(1) ion $[Cu(CN)2]-$ and perrheniate$[ReO4]-$.

5. A substantially uniform layer of micelle-metal ion complexes on a substrate comprising:
    the substrate;
    a block polymer comprising three or more blocks having two or more different types of ligands, with at least a first block having a first ligand and a second block having a second ligand; and
    two or more different types of metal ions attached to the two or more different types of ligands, wherein the metal ions are located substantially in a core of the micelle-metal complex,
    the micelle-metal ion complex being made from the block polymer having three or more blocks with at least two or more ligands attached thereto in the core of the micelle to which the two or more metal ions are attached.

6. The layer of claim 5, wherein the block polymer comprises an outer block, an inner block and at least one third block, wherein the outer and inner blocks are selected from the group consisting of polystyrene-poly(4-vinylpyridine), polystyrene-poly(2-vinylpyridine), polystyrene-poly(4-vinylphenol), poly(4-vinylpyridine-co-butylmethacrylate), poly(styrene-co-maleic acid) and poly(vinyl chloride-co-vinyl acetate-co-maleic acid).

7. The layer of claim 5, wherein two or more different types of ligands are present in said micelles in a specific ratio.

8. The layer of claim 5, wherein the one or more metal ions comprise at least one metal ion selected from the group consisting of $Ag^+$, $Cu^{2+}$, $Fe^{3+}$, $Al^{3+}$, $Pd^{2+}$, $Fe^{2+}$, $Ru^{3+}$, $Au^+$, $Au^{3+}$, cyclopentadienyl-iron-tricarbonyl $[CpFe(CO)_3]^+$, cyclopentadienyl-ruthenium-tricarbonyl $[CpRu(CO)_3]^+$, hexachlorostannate (IV) $[SnCl_6]^{2-}$, hexachlororhodate(III) $[RhCl_6]^{3-}$, permolybdate $[MoO_4]^{2-}$, dicyanocuprate(I) ion $[Cu(CN)_2]^-$, perrheniate$[ReO_4]^-$, tetrachloroaurate(III) $[AuCl_4]^{2-}$, dicyanideagenate (I) $[Ag(CN)_2]^-$, hexachloroplatinate $[PtCl_6]^{2-}$, and tetrahydroxoaluminate (III) $[Al(OH)_4]^-$.

9. The layer of claim 5, wherein one of the two or more different types of ligands comprises a crown ether.

10. The layer of claim 5, wherein the layer has a substantially uniform distribution of micelle size and ligand density.

11. The layer of claim 5, wherein the layer comprises a hexagonal array of micelle-metal ion complexes on the substrate surface.

* * * * *